United States Patent [19]

Klimesch et al.

[11] Patent Number: 5,163,994
[45] Date of Patent: Nov. 17, 1992

[54] CROP PROTECTION AGENT CONTAINING AN ACTIVE INGREDIENT

[75] Inventors: Roger Klimesch, Alsbach-Haehnlein; Adolf Parg, Bad Durkheim; Axel Sanner, Frankenthal; Winfried Angerer, Mannheim; Hans Theobald, Limburgerhof; Rainer Becker, Bad Durkheim; Peter Hofmeister, Neustadt; Christoph Kuenast, Otterstadt; Bernd Wolf, Mutterstadt, all of Fed. Rep. of Germany

[73] Assignee: BASF Aktiengesellschaft, Ludwigshafen, Fed. Rep. of Germany

[21] Appl. No.: 165,304

[22] Filed: Mar. 8, 1988

[30] Foreign Application Priority Data

Mar. 11, 1987 [DE] Fed. Rep. of Germany ....... 3707692
Mar. 14, 1987 [DE] Fed. Rep. of Germany ....... 3708297

[51] Int. Cl.$^5$ .......................................... A01N 43/02
[52] U.S. Cl. .......................................... 71/91; 71/118; 71/DIG. 1; 424/411; 428/907
[58] Field of Search .................... 71/1, 11, 27, 904, 65, 71/70, 79, 91, 118, DIG. 1; 521/29, 32, 33; 424/411; 428/907

[56] References Cited

U.S. PATENT DOCUMENTS 3,886,125 5/1975 Chromecek ..................... 71/904 X
4,217,417 8/1980 Smith ............................. 71/64.11 X
4,380,590 4/1983 Chong .................................. 521/33

FOREIGN PATENT DOCUMENTS 2919338 11/1980 Fed. Rep. of Germany ........ 71/904
849122 9/1960 United Kingdom .
1182886 3/1970 United Kingdom .

Primary Examiner—Ferris Lander
Attorney, Agent, or Firm—Keil & Weinkauf

[57] ABSTRACT

A crop protection agent containing an active ingredient and based on a polymeric carrier, the active ingredient being adsorbed onto, dissolved in or otherwise bound to the said carrier, contains, as the polymeric carrier, a macroporous crosslinked, preferably styrene-containing, polymer having a particle size such that the said agent can be distributed by means of a conventional apparatus for applying crop protection agents, the active ingredient being taken up in the carrier by absorption.

12 Claims, No Drawings

CROP PROTECTION AGENT CONTAINING AN ACTIVE INGREDIENT

The present invention relates to formulations of crop protection agents with delayed release of active ingredient (i.e. controlled-release formulations).

The use of crop protection agents in the form of a controlled-release formulations has many advantages over the conventional formulations, such as emulsion concentrates, suspension concentrates or wettable powders:

Since there are only small losses of active ingredient, the number of applications can be reduced.

In the case of soil application, controlled-release formulations prevent the active ingredient from being washed out into the ground water.

By reducing the application rates, any phytotoxic side effects of active ingredients can be substantially reduced.

Toxic compounds can be handled more safely in the controlled-release formulation, since the acute risk to the user is substantially reduced.

Readily volatile or easily decomposable (e.g. UV-unstable pyrethroids) active ingredients, for example natural substances can acquire a substantially more advantageous continuous action in a controlled-release formulation.

The following preparation processes for controlled-release formulations are known:

The simplest and best known method is the use of granules having an outer polymer shell. For this purpose, the active ingredient is first applied to a solid carrier which has a porous structure. Spraying a polymer onto the granules produces a layer which, as a result of the properties of the polymer, controls the release of the active ingredient. However, this type of controlled-release formulation is generally very expensive to prepare since a plurality of production steps have to be carried out, some involving the use of solvents. Furthermore, a constant release rate is achieved only when each granular particle is coated uniformly and completely. Moreover, in the case of some polymers used for producing the coating layer, the granules tend to agglomerate during storage. Use in practice is furthermore restricted to use as scattered granules. Thus, the only active ingredients which can be used are those which are suitable for soil treatment.

The monolithic systems provide another possible method of processing active ingredients in controlled-release formulations. Here, the active ingredients are homogeneously incorporated into polymer matrices. Depending on the chemical and physical properties of the polymer and of the active ingredient, this is done simply by dissolution or by suspension. To permit conversion to molding, the contents of active ingredients in the polymer matrices must, however, be kept low. Suitable moldings are granules, fibers or films. Because of the high proportion of polymer in these controlled-release formulations, use is often restricted to applications in which the polymer carrier can be completely disposed of. This type of formulation too may have an unsatisfactory shelf life since the active ingredients bloom, for example at high storage temperatures, and thus cause the moldings to stick together.

This disadvantage can be avoided if the active ingredients is chemically bonded to functional groups of the matrix system. However, the only active ingredients suitable for this purpose are those which themselves have an appropriate reactive group. This precondition greatly restricts the range of applications of this type of formulation. Another disadvantage is the relatively slow release of the active ingredient, this being due to the large amount of energy required to break the chemical bond. Such systems are suitable only for applications where a long continuous action is desired.

Another method for producing controlled-release formulations of active ingredients is microencapsulation. In this method, the active ingredient, as core material, is surrounded by an external polymer shell, which in turn permits a constant release rate. The microcapsules can be formulated in the form of an aqueous capsule suspension and, in this way, can be advantageously applied using a conventional sprayer.

However, microencapsulation has the following disadvantages:

Experience has shown that, for physical or chemical reasons, only a few active ingredients can be encapsulated.

Microencapsulation is technically relatively complicated, entailing corresponding costs.

In the production of the microcapsules, complete encapsulation of the active ingredient must be achieved. Furthermore, the capsules must be mechanically stable and capable of being stored.

The production of a homogeneous capsule suspension in an aqueous medium is complicated by pronounced agglomeration of the microcapsules or sedimentation or creaming.

It is an object of the present invention to provide formulations for active ingredients for crop protection, the said formulations being capable of being applied using conventional sprayers and releasing the active ingredients gradually in the desired amount. We have found that this object is achieved and that certain porous organic polymeric carriers are capable of holding a large number of active ingredients with retention of their activity and release them again slowly and uniformly without the active ingredient blooming during prolonged storage. These carriers can be prepared with a particle diameter of less than 300 μm and are therefore applied using conventional crop protection sprayers; they may hold 100% of their weight, or more, of crop protection agents and release them again uniformly over periods of from 2 weeks to 2 years, in any case within 4 weeks to 6 months.

The novel carrier is a macroporous crosslinked styrene or divinylbenzene polymer which is known per se and described, for example, by Brutskus et al., in Coll. J. USSR, 34 (1972), 438–442 or in British Patent 849,122.

The present invention relates to a crop protection agent containing an active ingredient and based on a polymeric carrier, the active ingredient being adsorbed onto, dissolved in or otherwise bound to the said carrier, and which contains, as the polymeric carrier, a macroporous crosslinked polystyrene or polydivinylbenzene having a particle size such that the said agent can be distributed by means of a conventional apparatus for applying crop protection agents, the active ingredient being taken up in the carrier by absorption.

In such an agent, the polymeric carrier contains
a) up to 100% by weight of divinylbenzene,
b) up to 95% by weight of styrene which may be monosubstituted or polysubstituted by $C_1$–$C_4$-alkyl, and c) up to 20% by weight of monomers which are copolymerizable with styrene and divinylbenzene.

Appropriate polymers which are prepared by free radical polymerization contain, as copolymerized units, preferably from 5 to 100, in particular from 5 to 25, % by weight of divinylbenzene, up to 95, preferably from 75 to 95, % by weight of styrene, which may furthermore be monosubstituted by $C_1$-$C_4$-alkyl in the α-position with respect to the nucleus or monosubstituted or poly-substituted by $C_1$-$C_4$-alkyl in the nucleus, and up t 20, preferably up to 10, % by weight of monomers which are copolymerizable with divinylbenzene and styrene, for example alkyl esters or hydroxyalkyl esters of acrylic or methacrylic acid, or styrenes having other substituents. Small amounts (up to 10% by weight) of water-soluble monomers, e.g. acrylic acid, methacrylic acid or vinylimidazole, may also be incorporated. The particularly preferred polymers consist of from 10 to 25% by weight of industrial divinylbenzene (containing about 50% of divinylbenzene, the remainder being predominantly ethylstyrene, as well as small amounts of trivinylbenzene, etc.) and from 75 to 90% by weight of styrene.

Polymerization of the monomer (mixture) is carried out in the form of a suspension polymerization using water as the outer phase, a particle diameter of from 80 to 300 μm, preferably from 100 to 200 μm, being desired. This is achieved, for example, by using an impeller stirrer. A pore former is used to make the polymer macroporous. A suitable pore former is a liquid which does not interfere with the polymerization, is water-immiscible and dissolves the monomer but at most only slightly swells the polymer; examples of suitable substances are alkanes of 7 to 12 carbon atoms, preferably n-octane, or gasolines having a boiling point of not less than 100° C. The amount of pore former is, for example, from 50 to 400% by weight, based on the monomers. The upper limit of the amount of pore former is determined by the mechanical properties of the polymer and depends on the particular pore former.

The polymer suspension obtained is washed with water and subjected to the usual working up measures; finally, the pore former and any adhering water is removed after the polymerization, by drying the polymers under reduced pressure at 50° C. The dried polymers are advantageously stored in sealed containers to prevent them from absorbing either water or other substances from the environment.

For the purposes of the present invention, the active ingredients used can in principle be compounds or mixtures of compounds having any type of action.

Examples of insecticides are phosphates, carbamates, halohydrocarbons and pyrethroids.

Examples of herbicides are phenoxy fatty acids, diphenyl ethers, phenol derivatives, aniline derivatives, urea derivatives, carbamates, triazine compounds and compounds of cyclohexenone and of pyridazone.

Examples of fungicides are metal-containing, sulfur-containing or other inorganic or organic compounds, such as dithiocarbamates, disulfides, nitro compounds, heterocyclic substances and halogenated compounds.

The invention can furthermore advantageously be used for formulating or fixing active ingredients in the wider sense, for example pheromones, repellents, synergistic agents, wood preservatives, preservatives, growth regulators, rodenticides and similar agents which can be used in agriculture.

If the active ingredients are liquid, active ingredients, or mixtures of these, for crop protection are taken up by diluting them, if necessary, and mixing them thoroughly with the novel polymeric carriers in a sealed vessel for about 0.5-2 hours. If the active ingredients are solid or pasty at room temperature, they are dissolved in suitable organic agents, mixed in the form of a solution with the carriers and further treated as described above. These solvents may remain in the carrier or may be removed from the carrier again, for example by drying.

The particular advantage of these formulations is that they are finely divided and can therefore be formulated as a wettable powder. This has the following advantages for use in practice:

The formulations, which release active ingredients slowly, can be applied in this form using conventional sprayers.

Conventional spraying permits application in combination with other commercial formulations of active ingredients and of fertilizers.

To prepare a wettable powder using the novel formulations, the latter are advantageously homogenized together with wetting agents, dispersants and adhesion promoters, and if necessary also fillers.

Suitable wetting agents, dispersants and adhesion promoters are surfactants, such as alkali metal, alkaline earth metal and ammonium salts of ligninsulfonic acids, naphthalenesulfonic acids, phenolsulfonic acids, alkylarylsulfonic acids, alkylsulfonates, alkylsulfates, alkali metal and alkaline earth metal salts of dibutylnaphthalic acid, and condensates of sulfonated alkylnaphthalenesulfonic acids with phenol, formaldehyde and urea.

Suitable fillers are kaolins, silicas, chalks, bentonites, silica gels, clays, calcium sulfate, magnesium sulfate, talc, magnesium oxide, lime and all solid, water-insoluble materials.

The Examples which follow describe experiments on evaporation of active ingredients; the carriers provided with the active ingredient were applied to filter paper strips and suspended for several weeks in well ventilated rooms. Samples of the strips were taken at intervals of 7 days and investigated for residual content of active ingredient.

PREPARATION EXAMPLES FOR THE POLYMERIC CARRIER USED ACCORDING TO THE INVENTION

Example A

An emulsion consisting of 150 g of styrene, 50 g of industrial divinylbenzene (containing about 50% of ethylvinylbenzene), 200 g of n-octane, 1 g of lauryl peroxide, 1 g of polyvinylpyrrolidone having a K value of 90, as a suspending agent, and 1,300 ml of water is stirred for 8 h at 85° C. under nitrogen at a stirrer speed of 400 rpm. The resulting macroporous bead polymer having a bead diameter of from 100 to 200 μm is washed with water and dried at 50° C. under reduced pressure (<30 mbar). 195.0 g (97.5% by weight of the theoretical amount) are obtained.

Example B

A bead polymer is prepared using 180 g of styrene, 20 g of industrial divinyl benzene (containing about 50% of ethylvinylbenzene), 200 g of n-octane, 1 g of lauryl peroxide, 1,300 ml of water and 2 g of polyvinylpyrrolidone having a K value of 90, as a suspending agent, nitrogen being passed in and the polymerization being carried out for 8 h at 85° C. and at a stirrer speed of 400 revolutions per hour. The resulting bead polymer having a bead diameter of from 100 to 300 μm is washed with water and dried at 50° C. under reduced pressure. Yield: 190.0 g (95%).

EXAMPLE C

An emulsion consisting of 160 g of styrene, 20 g of industrial divinylbenzene (containing about 50% of ethylvinylbenzene), 20 g of methacrylic acid, 200 g of n-octane, 1 g of lauryl peroxide, 3 g of polyvinylpyrrolidone having a K value of 90, as a suspending agent, and 1,300 ml of water is stirred for 8 h at 90° C. under nitrogen at a stirrer speed of 400 rpm. The resulting bead polymer having a bead diameter of from 100 to 200 μm is washed with water and dried at 50° C. under reduced pressure.
Yield: 196.0 g (98%).

EXAMPLE D

An emulsion consisting of 135 g of styrene, 45 g of industrial divinylbenzene (containing about 50% of ethylvinylbenzene), 20 g of dimethylaminoethyl methacrylate, 200 g of n-octane, 1 g of lauryl peroxide, 1 g of polyvinylpyrrolidone having a K value of 90, as a suspending agent, and 1,300 ml of water is stirred for 8 h at 90° C. under nitrogen at a stirrer speed of 450 rpm. The resulting bead polymer having a bead diameter of from 100 to 250 μm is washed with water and dried at 50° C. under reduced pressure (<30 mbar). Yield: 192.0 g (96%).

EXAMPLE E

An emulsion consisting of 160 g of styrene, 20 g of industrial divinylbenzene (containing about 50% of ethylvinylbenzene), 20 g of hydroxyethyl methacrylate, 200 g of n-octane, 1 g of lauryl peroxide, 1 g of polyvinylpyrrolidone having a K value of 90, as a suspending agent, and 1,300 ml of water is stirred for 8 h at 90° C. under nitrogen at a stirrer speed of 400 rpm. The resulting bead polymer having a bead diameter of from 100 to 300 μm is washed with water and dried at 50° C. under reduced pressure. Yield: 192.0 g (96%).

PREPARATION EXAMPLES FOR THE AGENTS ACCORDING TO THE INVENTION

EXAMPLE 1

100 g of a polymer corresponding to Example A and 100 g of the herbicide metolachlor are combined, and mixed thoroughly in a sealed vessel for ½ hour. The resulting herbicide-containing particles retain their original size, do not swell in water, are dry on the surface and are free-flowing.

EXAMPLE 2

100 g of a polymer corresponding to Example B and 200 g of the fungicide tridemorph are combined, and mixed thoroughly in a sealed vessel for ½ hour. The resulting fungicide-containing particles retain their original size, do not swell in water, are dry on the surface and are free-flowing.

EXAMPLE 3

100 g of a polymer corresponding to Example D and 100 g of the fungicide fenpropimorph are combined, and mixed thoroughly in a sealed vessel for ½ hour. The resulting particles retain their original size, do not swell in water, are dry on the surface and are free-flowing.

EXAMPLE 4

100 g of a polymer corresponding to Example E and 100 g of the fungicide furmecylcox are combined, and mixed thoroughly in a sealed vessel for ½ hour. The resulting particles retain their original size, do not swell in water, are dry on the surface and are free-flowing.

EXAMPLE 5

100 g of a polymer corresponding to Example B and 250 g of a solution consisting of 100 g of the herbicide bentazon and 150 g of dimethylformamide are combined, and thoroughly mixed in a sealed vessel for ½ hour. This mixture is dried for 4 h under 1 mbar and at a bath temperature of 40° C. in order to remove the solvent. The resulting herbicide-containing particles retain their original size, do not swell in water, are dry on the surface and are free-flowing.

EXAMPLES OF AGENTS FORMULATED ACCORDING TO THE INVENTION

EXAMPLE 6

100 g of the carrier according to Preparation Example 1, containing active ingredient, are mixed for 30 minutes, in a laboratory mixer operating according to the Lödige principle (plowshare mixer), with 75 g of the sodium salt of a phenosulfonic acid/urea/formaldehyde condensate (commercial name Wettol D 1), 75 g of Wettol D 2 (phenol/formaldehyde/sodium sulfite condensate), 100 g of Wettol NT 1 (sodium alkylnaphthalenesulfonate) and 650 g of chalk. The end product has a suspendibility (measured according to CIPAC-MT 15 at a spray liquor concentration of 0.5% after 30 minutes) of about 75%, and of about 70% after 60 minutes.

EXAMPLE 7

200 g of the carrier according to Example 2, containing active ingredient, are mixed for 60 minutes, in a Lödige mixer, with 100 g of Wettol D 1, 75 g of Wettol SSP, 150 g of Wettol NT 1 and 475 g of chalk. The end product has a suspendibility (at a spray liquor concentration of 0.25% after 30 minutes) of about 77%, and of about 72% after 60 minutes.

EXAMPLE 8

100 g of the carrier according to Example 3, containing active ingredient, are mixed for 45 minutes, in a Lödige mixer, with 75 g of Wettol D 1, 150 g of Wettol SSP, 100 g of Wettol NT 1 and 575 g of chalk. The end product has a suspendibility (at a spray liquor concentration of 0.5% after 30 minutes) of about 73%, and of about 69% after 60 minutes.

EXAMPLE 9

200 g of the carrier according to Example 3, containing active ingredient, are mixed for 60 minutes, in a Lödige mixer, with 75 g of Wettol D 1, 50 g of Zewa Na (ligninsulfonate), 75 g of Wettol SSP, 100 g of Wettol NT 1 and 500 g of kaolin. The end product has a suspendibility (at a spray liquor concentration of 0.25% after 30 minutes) of about 78%, and of about 72% after 60 minutes.

EXAMPLES 10 AND 11

A Pyrethroid-containing Agent 100 g of one of the carriers described above and 200 g of a solution of 100 g of the pyrethroid in 100 g of tetrahydrofuran are mixed thoroughly for 30 minutes, after which the solvent is removed from the mixture in the course of 4 hours under 1 mbar and at 40° C. The pyrethroid of Example 10 is mixed with the carrier of Preparation Example A, and the pyrethroid of Example 11 is mixed with the carrier E.

TABLE

| Polymer of Example | | Pyrethroid |
|---|---|---|
| 10 | A | (structure: dichlorovinyl cyclopropane carboxylate, furan-CH₂, 4-fluorophenyl) |
| 11 | E | (structure: dichlorovinyl cyclopropane carboxylate, furan-CH₂, phenyl) |

Further Examples of the preparation of formulations of active ingredients

EXAMPLE 12

100 g of the pyrethroid-containing carrier from Example 10 are mixed for 30 minutes, in a laboratory mixer operating according to the Lödige principle (plowshare mixer), with 75 g of the sodium salt of a phenolsulfonic acid/urea/formaldehyde condensate (commercial name Wettol D1), 75 g of Wettol D 2 (phenol/formaldehyde/sodium sulfite condensate), 100 g of Wettol NT 1 (sodium alkylnaphthalenesulfonate) and 650 g of chalk. The end product has a suspendibility (measured according to CIPAC-MT 15 at a spray liquor concentration of 0.5 % after 30 minutes) of about 79%, and of about 73% after 60 minutes.

EXAMPLE 13

200 g of the pyrethroid-containing carrier from Example 11 are mixed for 60 minutes, in a Lödige mixer, with 100 g of Wettol D 1, 75 g of Wettol SSP, 150 g of Wettol NT 1 and 475 g of chalk. The end product has a suspendibility (at a spray liquor concentration of 0.25% after 30 minutes) of about 80%, and of about 75% after 60 minutes.

EXAMPLE 14

100 g of the pyrethroid-containing carrier from Example 12 are mixed for 45 minutes, in a Lödige mixer, with 75 g of Wettol D 1, 150 g of Wettol SSP, 100 g of Wettol NT 1 and 575 g of chalk. The end product has a suspendibility (at a spray liquor concentration of 0.5% after 30 minutes) of about 76%, and of about 72% after 60 minutes.

EXAMPLE 15

200 g of the pyrethroid-containing carrier from Example 12 are mixed for 60 minutes, in a Lödige mixer, with 75 g of Wettol D 1, 50 g of Zewa Na (ligninsulfonate), 75 g of Wettol SSP, 100 g of Wettol NT 1 and 500 g of kaolin. The end product has a suspendibility (at a spray liquor concentration of 0.25% after 30 minutes) of about 77%, and of about 74% after 60 minutes.

EXAMPLE OF USE

Musca Domestica—Continuous Action on Glass Plates

The samples are applied uniformly to roughened glass plates measuring 15×15 cm. 10 houseflies are introduced onto each of the dried coatings, under a Petri dish (diameter about 9 cm), and the effect is rated after 4 hours. The experiment is repeated daily until the effect has disappeared. The plates are stored at room temperature (about 22° C.). The test is carried out twice, 1 mg of active ingredient being used per plate, once in the formulation according to the invention and, for comparison purposes, once in conventional solution in acetone.

TABLE

| Active ingredient of Example | Formulation used | Number of days | Mortality [%] |
|---|---|---|---|
| 10 | 0.1% strength by weight acetone solution (not stabilized; Comparison) | 1 | 100 |
| | | 2 | 0 |
| 10 | According to Example 12 (stabilized) | 7 | 90 |
| 11 | 0.1% strength by weight acetone solution (not stabilized; Comparison) | 1 | 100 |
| | | 2 | 0 |
| 11 | According to Example 12 (stabilized) | 6 | 90 |

EXAMPLE 16

100 g of a polymer corresponding to Example A and 100 g of Z-9-dodecenyl acetate (pheromone of the grapeberry moth) are combined, and mixed thoroughly in a sealed vessel for ½ hour. The resulting pheromone-containing particles retain their original size, do not swell in water, are dry on the surface and are free-flowing.

EXAMPLE 17

100 g of a polymer corresponding to Example B and 200 g of Z-9-dodecenyl acetate (pheromone of the grapeberry moth) are combined, and mixed thoroughly in a tightly closed vessel for ½ hour. The resulting pheromone-containing particles retain their original size, do not swell in water, are dry on the surface and are free-flowing.

EXAMPLE 18

100 g of a polymer corresponding to Example D and 100 g of a 1:1 mixture of Z-7,Z-9-hexadecadienyl acetate and Z-9,E-9-hexadecadienyl acetate (pheromone of the pink bollworm) are combined, and mixed thoroughly in a sealed vessel for ½ hour. The resulting pheromone-containing particles retain their original size, do not swell in water, are dry on the surface and are free-flowing. Comparison of the evaporation behavior of novel formulations containing Z-9-dodecenyl acetate (Z9-DDA) and consisting of one of the novel agents with that of the release system disclosed in German Laid-Open Application DOS 2,740,497.

TABLE

| Time [weeks] | Residual pheromone content in the carrier [%] | | |
|---|---|---|---|
| | Example 16 | Example 17 | Carrier film according to DOS 2,740,497 |
| 0 | 100 | 100 | 100 |
| 1 | 87 | 76 | 80 |
| 2 | 73 | 64 | 67 |
| 3 | 65 | 52 | 54 |
| 4 | 52 | 35 | 50 |
| 5 | 45 | 24 | 37 |
| 6 | 32 | 16 | 33 |
| 7 | 26 | 10 | 24 |

We claim:

1. A crop protection agents with delayed release of active ingredient consisting essentially of a polymer carrier and an active ingredient absorbed in the carrier without chemical bonding, said polymer carrier being a macroporous crosslinked polystyrene or polydivinyl benzene containing copolymerizable units of the following monomers:
    a) from 5 to 100% by weight of divinyl benzene,
    b) up to 95% by weight of styrene which may be monosubstituted or polysubstituted by $C_1-C_4$-alkyl,
    c) up to 20% by weight of monomers which are copolymerizable with styrene and divinyl benzene, and
    d) up to 10% by weight of water soluble monomers said polymer having no chelating groups and having a particle size such that the agent can be distributed by means of a conventional apparatus for applying crop protection agents; the active ingredient being at least one of the following:
    a) an insecticide,
    b) an herbicide,
    c) a fungicide,
    e) a pheromone,
    f) a wood preservative, and
    h) a rodenticide.

2. An agent as defined in claim 1, in which the particles of the macroporous polymeric carrier have a diameter of from 80 μm to 300 μm.

3. An agent as defined in claim 1, which is obtainable by taking up the active ingredient in the macroporous polymeric carrier at room temperature.

4. An agent which is obtainable by formulating an agent according to claim 1 together with wetting agents, dispersants, adhesion promoters and, if required, fillers to give a wettable powder.

5. A crop protection agents as defined in claim 1, wherein the active ingredient is a pheromone.

6. A crop protection agent as defined in claim 1, wherein the active ingredient is a pyrethroid.

7. A crop protection agent as defined in claim 1, wherein the active ingredient is a fungicide.

8. An agent as defined in claim 1, in which said macroporous polymeric carrier is formed by suspension polymerization in the presence of a pore former.

9. A crop protection agent as defined in claim 1, wherein said carrier holds at least 100% of its weight of active ingredient.

10. A crop protection agent with delayed release of an active ingredient consisting essentially of a polymer carrier and an active ingredient absorbed in the carrier without chemical bonding, said polymer carrier being a macroporous crosslinked polystyrene or polydivinylbenzene formed by suspension polymerization in the presence of a pore former and having a particle diameter of from 80 μm to 300 μm and which consists essentially of
    a) from 5 to 100% by weight of divinylbenzene,
    b) up to 95% by weight of styrene which may be monosubstituted or polysubstituted by $C_1-C_4$-alkyl,
    c) up to 20% by weight of monomers which are copolymerizable with styrene and divinyl benzene, and
    d) up to 10% by weight of water soluble monomers.

11. A crop protection agent as defined in claim 10, wherein the active ingredient is selected from the group consisting of a pheromone, a pyrethroid or a fungicide.

12. A crop protection agent as defined in claim 10, wherein said carrier holds at least 100% of its weight of active ingredient.

* * * * *

UNITED STATES PATENT AND TRADEMARK OFFICE
CERTIFICATE OF CORRECTION

PATENT NO. : 5,163,994

DATED : NOV. 17, 1992

INVENTOR(S) : KLIMESCH et al.

It is certified that error appears in the above-identified patent and that said Letters Patent is hereby corrected as shown below:

in claim 1, column 9, line 37: "protection agents with"

should read --protection agent with--

Signed and Sealed this

Twenty-sixth Day of October, 1993

Attest:

BRUCE LEHMAN

Attesting Officer

Commissioner of Patents and Trademarks